US008663694B2

(12) United States Patent
Brück-Scheffler et al.

(10) Patent No.: US 8,663,694 B2
(45) Date of Patent: Mar. 4, 2014

(54) TASTE MASKED DOSAGE FORM CONTAINING ROFLUMILAST

(75) Inventors: Antje Brück-Scheffler, Constance (DE); Alexander Pontius, Lebach (DE)

(73) Assignee: Takeda GmbH, Konstanz (DE)

( * ) Notice: Subject to any disclaimer, the term of this patent is extended or adjusted under 35 U.S.C. 154(b) by 1308 days.

(21) Appl. No.: 11/885,837

(22) PCT Filed: Mar. 14, 2006

(86) PCT No.: PCT/EP2006/060679
§ 371 (c)(1),
(2), (4) Date: Sep. 7, 2007

(87) PCT Pub. No.: WO2006/097456
PCT Pub. Date: Sep. 21, 2006

(65) Prior Publication Data
US 2008/0193544 A1 Aug. 14, 2008

(30) Foreign Application Priority Data
Mar. 16, 2005 (EP) .................................. 05102058

(51) Int. Cl.
*A61K 9/14* (2006.01)
*A61K 9/16* (2006.01)
*A61K 9/20* (2006.01)
*A61K 9/48* (2006.01)

(52) U.S. Cl.
USPC ............ 424/489; 424/451; 424/464; 424/490

(58) Field of Classification Search
None
See application file for complete search history.

(56) References Cited

U.S. PATENT DOCUMENTS

| | | | |
|---|---|---|---|
| 3,065,142 A | 11/1962 | Antonides |
| 4,006,227 A | 2/1977 | Gallegos et al. |
| 4,024,240 A | 5/1977 | Thakkar |
| 4,343,804 A | 8/1982 | Munson et al. |
| 4,349,563 A | 9/1982 | Gilbert et al. |
| 4,450,164 A | 5/1984 | Bristol et al. |
| 4,464,372 A | 8/1984 | Bristol et al. |
| 4,563,455 A | 1/1986 | Ueda et al. |
| 4,621,084 A | 11/1986 | Takaya et al. |
| 4,686,227 A | 8/1987 | Ueda et al. |
| 4,725,601 A | 2/1988 | Ueda et al. |
| 4,753,945 A | 6/1988 | Gilbard et al. |
| 4,769,384 A | 9/1988 | Kise et al. |
| 4,782,055 A | 11/1988 | Ueda et al. |
| 4,791,117 A | 12/1988 | Press |
| 4,806,550 A | 2/1989 | Ife et al. |
| 4,831,041 A | 5/1989 | Shiokawa et al. |
| 4,833,149 A | 5/1989 | Press |
| 4,839,353 A | 6/1989 | Hosoi et al. |
| 4,900,775 A | 2/1990 | Smith et al. |
| 4,920,129 A | 4/1990 | Shiokawa et al. |
| 5,006,595 A | 4/1991 | Smith et al. |
| 5,011,843 A | 4/1991 | Shell |
| 5,041,442 A | 8/1991 | Romero et al. |
| 5,051,508 A | 9/1991 | Brown et al. |
| 5,089,504 A | 2/1992 | Ife et al. |
| 5,102,892 A | 4/1992 | Geiss et al. |
| 5,112,834 A | 5/1992 | Senn |
| 5,188,838 A | 2/1993 | Deleuil et al. |
| 5,200,417 A | 4/1993 | Brown et al. |
| 5,215,999 A | 6/1993 | Uchida et al. |
| 5,252,580 A | 10/1993 | Takahashi et al. |
| 5,262,171 A | 11/1993 | Login et al. |
| 5,286,494 A | 2/1994 | Fechner et al. |
| 5,320,848 A | 6/1994 | Geyer et al. |
| 5,326,879 A | 7/1994 | Takahashi et al. |
| 5,340,827 A | 8/1994 | Beeley et al. |
| 5,380,532 A | 1/1995 | Deleuil et al. |
| 5,409,943 A | 4/1995 | Ife et al. |
| 5,429,824 A | 7/1995 | June |
| 5,439,917 A | 8/1995 | Briving et al. |
| 5,534,515 A | 7/1996 | Grundler |
| 5,665,730 A | 9/1997 | Senn et al. |
| 5,677,302 A | 10/1997 | Karimian et al. |
| 5,686,458 A | 11/1997 | Lee et al. |
| 5,698,711 A | 12/1997 | Palfreyman |
| 5,712,298 A | 1/1998 | Amschler |
| 5,719,161 A | 2/1998 | Rainer |
| 5,762,953 A | 6/1998 | Venkateshwaran |
| 5,824,687 A | 10/1998 | Senn |
| 5,891,904 A | 4/1999 | Stief et al. |
| 5,972,381 A | 10/1999 | Sangekar et al. |
| 5,972,927 A | 10/1999 | Pascal et al. |
| 6,114,537 A | 9/2000 | Karimian et al. |
| 6,124,313 A | 9/2000 | Grundler et al. |

(Continued)

FOREIGN PATENT DOCUMENTS

CA 2016141 11/1990
CA 2497176 3/2004

(Continued)

OTHER PUBLICATIONS

Glenn M. Roy, "Taste Masking in Oral Pharmaceuticals." pp. 24-35 (1994).
Anonymous, "Masking the taste of fast-disintegrating tablets." Innovations in Pharmaceutical Technologies, v.4, pp. 109-111 (2004).
"Glossary", *Ph Eur Monograph*, 2005, 1502:1-2.
"Remington: The Science and Practice of Pharmacy", vol. II, Mack Publishing: Company: Easton, Pennsylvania, 1995, p. vii-viii and 1618-1629.
Academic book Applied Pharmacy Farmacja Stosowana Fiebig Janicki, 2001, pp. 267-268.
Ammar et al., "Improvement of the biological performance of oral anticoagulant drugs", 1997, Pharmazie 52: 627-631.
Antoni et al., "Synthesis of [18F] Labelled Roflumilast Using Difluoro [18F] Bromomethane as Alkylating Agent," *Synthesis and Applications of Isotopically Labeled Compounds,* 2000, 7:375-376.
Assmann S F Lancet 2000 vol. 355 p. 1064-69.
Baraniuk et al., "Inhibition of Phosphodiesterase 4 in Allergic Rhinitis", (Review of Schmidt et al., J Allergy Clin Immunol, 2001, 108:530-536, Clinical Trials Report, pp. 191-193.
Barsig et al., "Protection by the Phosphodiesterase-4 Inhibitor Roflumilast of Mice Against Collagen-induced Arthritis," 2001, Poster Presentation, 1 page.

(Continued)

*Primary Examiner* — Susan Tran
(74) *Attorney, Agent, or Firm* — Nath, Goldberg & Meyer; Sheldon M. McGee

(57) ABSTRACT

Taste masked dosage forms for oral administration of roflumilast are described.

21 Claims, No Drawings

(56) References Cited

U.S. PATENT DOCUMENTS

| | | |
|---|---|---|
| 6,132,770 A | 10/2000 | Lundberg |
| 6,160,119 A | 12/2000 | Senn |
| 6,174,878 B1 | 1/2001 | Gamache et al. |
| 6,218,400 B1 | 4/2001 | Daugan et al. |
| 6,231,885 B1 | 5/2001 | Carrara |
| 6,255,326 B1 | 7/2001 | Ashton |
| 6,258,833 B1 | 7/2001 | Martins et al. |
| 6,265,415 B1 | 7/2001 | Amin et al. |
| 6,270,807 B1 | 8/2001 | Danielson et al. |
| 6,288,118 B1 | 9/2001 | Niemann et al. |
| 6,313,136 B1 | 11/2001 | Amin et al. |
| 6,313,137 B1 | 11/2001 | Amin et al. |
| 6,328,993 B1 | 12/2001 | Linder et al. |
| 6,348,602 B1 | 2/2002 | Fowler et al. |
| 6,375,968 B1 * | 4/2002 | Quong .................. 424/408 |
| 6,379,682 B1 | 4/2002 | Tchinnis et al. |
| 6,383,510 B1 | 5/2002 | Linder et al. |
| 6,384,048 B1 | 5/2002 | Senn |
| 6,417,190 B1 | 7/2002 | Hoffmann et al. |
| 6,432,451 B1 * | 8/2002 | Lee et al. ............. 424/490 |
| 6,436,952 B1 | 8/2002 | Flockerzi |
| 6,436,970 B1 | 8/2002 | Hafner et al. |
| 6,448,274 B2 | 9/2002 | Friesen et al. |
| 6,498,173 B1 | 12/2002 | Kilian |
| 6,503,923 B1 | 1/2003 | Senn |
| 6,531,493 B1 | 3/2003 | Kley et al. |
| 6,537,983 B1 | 3/2003 | Biggadike et al. |
| 6,555,583 B2 | 4/2003 | Nieman et al. |
| 6,579,884 B1 | 6/2003 | Amin et al. |
| 6,613,775 B1 | 9/2003 | Amin et al. |
| 6,624,181 B1 | 9/2003 | Kilian et al. |
| 6,630,161 B1 | 10/2003 | Leesman |
| 6,670,394 B1 | 12/2003 | Christensen et al. |
| 6,677,362 B1 | 1/2004 | Ghebre et al. |
| 6,743,443 B1 | 6/2004 | Furitsu et al. |
| 6,767,557 B2 | 7/2004 | Ulrich et al. |
| 6,822,114 B1 | 11/2004 | Williams et al. |
| 6,872,382 B1 | 3/2005 | Gamache et al. |
| 6,897,229 B2 | 5/2005 | Kilian |
| 7,056,936 B2 | 6/2006 | Kilian et al. |
| 7,147,869 B2 | 12/2006 | Dietrich et al. |
| 7,175,854 B2 | 2/2007 | Dietrich et al. |
| 7,182,958 B1 | 2/2007 | Oren et al. |
| 7,357,943 B2 | 4/2008 | Linder et al. |
| 7,393,860 B1 | 7/2008 | Senn-Bilfinger |
| D580,547 S | 11/2008 | Lolis et al. |
| 7,745,646 B2 | 6/2010 | Govek et al. |
| 7,785,630 B2 | 8/2010 | Dietrich et al. |
| 7,790,198 B2 | 9/2010 | Dietrich et al. |
| 7,794,752 B1 | 9/2010 | Dietrich et al. |
| 7,927,623 B2 | 4/2011 | Sugimoto et al. |
| 7,951,397 B2 | 5/2011 | Dietrich et al. |
| 7,951,398 B2 | 5/2011 | Dietrich et al. |
| 2001/0044409 A1 | 11/2001 | Ghebre et al. |
| 2002/0002191 A1 | 1/2002 | Friesen |
| 2002/0006418 A1 | 1/2002 | Kung et al. |
| 2002/0086039 A1 | 7/2002 | Lee et al. |
| 2002/0193393 A1 | 12/2002 | Pairet et al. |
| 2003/0018071 A1 | 1/2003 | Rennard et al. |
| 2003/0092706 A1 | 5/2003 | Barsig |
| 2003/0099700 A1 * | 5/2003 | Faham et al. ............. 424/465 |
| 2003/0195233 A1 | 10/2003 | Magee |
| 2003/0207845 A1 | 11/2003 | Keating et al. |
| 2003/0212112 A1 | 11/2003 | Murdoch et al. |
| 2004/0024007 A1 | 2/2004 | Pairet et al. |
| 2004/0058896 A1 * | 3/2004 | Dietrich et al. ............. 514/171 |
| 2004/0058950 A1 | 3/2004 | Meade et al. |
| 2004/0101558 A1 | 5/2004 | Dietrich et al. |
| 2004/0151722 A1 | 8/2004 | Banerjee et al. |
| 2004/0241235 A1 | 12/2004 | Lebon et al. |
| 2005/0159492 A1 | 7/2005 | Dietrich et al. |
| 2006/0069155 A1 | 3/2006 | Edelson et al. |
| 2006/0084684 A1 | 4/2006 | Bolle et al. |
| 2006/0084685 A1 | 4/2006 | Koenen et al. |
| 2006/0105038 A1 | 5/2006 | Lai et al. |
| 2006/0142308 A1 | 6/2006 | Kolassa et al. |
| 2006/0147382 A1 | 7/2006 | Bundschuh et al. |
| 2006/0159758 A1 | 7/2006 | Gandhi et al. |
| 2006/0198889 A1 * | 9/2006 | Sandhu et al. ............. 424/470 |
| 2006/0199865 A1 | 9/2006 | Beume et al. |
| 2006/0228410 A1 | 10/2006 | Dumont et al. |
| 2006/0269600 A1 | 11/2006 | Dietrich |
| 2007/0122474 A1 | 5/2007 | Dietrich |
| 2007/0134729 A1 | 6/2007 | Christensen et al. |
| 2007/0254928 A1 | 11/2007 | Wollin et al. |
| 2008/0193544 A1 | 8/2008 | Bruck-Scheffler et al. |
| 2008/0280958 A1 | 11/2008 | Bolle et al. |
| 2010/0310477 A1 | 12/2010 | Pairet et al. |
| 2011/0060016 A1 | 3/2011 | Dietrich et al. |
| 2011/0212182 A1 | 9/2011 | Lebon et al. |
| 2011/0251244 A1 | 10/2011 | Dietrich et al. |
| 2011/0313005 A1 | 12/2011 | Bolle et al. |

FOREIGN PATENT DOCUMENTS

| | | |
|---|---|---|
| CN | 1126468 | 11/2003 |
| CN | 1189832 | 2/2005 |
| DE | 3011490 | 3/1981 |
| DE | 3622036 | 1/1987 |
| DE | 3917232 | 11/1990 |
| DE | 3943385 | 7/1991 |
| DE | 69101493 | 8/1994 |
| DE | 10061137 | 6/2002 |
| DE | 19925710 | 10/2002 |
| EP | 33094 | 8/1981 |
| EP | 68378 | 1/1983 |
| EP | 120589 | 10/1984 |
| EP | 125756 | 11/1984 |
| EP | 165545 | 12/1985 |
| EP | 228006 | 7/1987 |
| EP | 261912 | 3/1988 |
| EP | 264883 | 4/1988 |
| EP | 266890 | 5/1988 |
| EP | 268989 | 6/1988 |
| EP | 308917 | 3/1989 |
| EP | 163965 | 11/1989 |
| EP | 368158 | 5/1990 |
| EP | 120352 | 6/1990 |
| EP | 438359 | 7/1991 |
| EP | 399267 | 12/1991 |
| EP | 204285 | 1/1992 |
| EP | 259174 | 3/1992 |
| EP | 307078 | 8/1992 |
| EP | 509974 | 10/1992 |
| EP | 510562 | 10/1992 |
| EP | 330485 | 5/1993 |
| EP | 563024 | 9/1993 |
| EP | 387821 | 8/1994 |
| EP | 393926 | 9/1994 |
| EP | 617612 | 10/1994 |
| EP | 537532 | 11/1996 |
| EP | 535529 | 7/1997 |
| EP | 1118615 | 7/2001 |
| EP | 1161950 | 12/2001 |
| EP | 1187601 | 3/2002 |
| EP | 1105390 | 6/2003 |
| EP | 1 366 760 A1 | 12/2003 |
| EP | 1199074 | 4/2004 |
| EP | 1120120 | 4/2009 |
| EP | 1478399 | 3/2012 |
| ES | 2176252 | 12/2002 |
| JP | 61205208 | 9/1986 |
| JP | 2270873 | 11/1990 |
| JP | 2049720 | 12/1990 |
| JP | 3284622 | 12/1991 |
| JP | 3284686 | 12/1991 |
| JP | 4212359 | 8/1992 |
| JP | 5271070 | 10/1993 |
| JP | 3031280 | 11/1996 |
| JP | 8-512041 | 12/1996 |
| JP | 9059152 | 3/1997 |
| JP | 11152224 | 6/1999 |
| JP | 2000516633 | 12/2000 |
| JP | 20086502 | 7/2009 |

(56) References Cited

FOREIGN PATENT DOCUMENTS

| | | |
|---|---|---|
| KR | 2000-0029011 | 5/2000 |
| KR | 100331255 | 10/2002 |
| PL | 178314 | 1/1995 |
| WO | 8900570 | 1/1989 |
| WO | 8908127 | 9/1989 |
| WO | 9114677 | 10/1991 |
| WO | 9117164 | 11/1991 |
| WO | 9118887 | 12/1991 |
| WO | 9206979 | 4/1992 |
| WO | 9212961 | 8/1992 |
| WO | 9212969 | 8/1992 |
| WO | 9221328 | 12/1992 |
| WO | 9308190 | 4/1993 |
| WO | 9312090 | 6/1993 |
| WO | 9315055 | 8/1993 |
| WO | 9315056 | 8/1993 |
| WO | 9315071 | 8/1993 |
| WO | 9325517 | 12/1993 |
| WO | 9402465 | 2/1994 |
| WO | 9414795 | 7/1994 |
| WO | 9424130 | 10/1994 |
| WO | 95/01338 A1 | 1/1995 |
| WO | 9527714 | 10/1995 |
| WO | 9617830 | 6/1996 |
| WO | 9725030 | 7/1997 |
| WO | 9736905 | 10/1997 |
| WO | 9807400 | 2/1998 |
| WO | 9820858 | 5/1998 |
| WO | 9835683 | 8/1998 |
| WO | 9837080 | 8/1998 |
| WO | 9842707 | 10/1998 |
| WO | 9854188 | 12/1998 |
| WO | 9929299 | 6/1999 |
| WO | 9955705 | 11/1999 |
| WO | 9955706 | 11/1999 |
| WO | 9963940 | 12/1999 |
| WO | 0010999 | 3/2000 |
| WO | 0012501 | 3/2000 |
| WO | 0017200 | 3/2000 |
| WO | 0018388 | 4/2000 |
| WO | 0026217 | 5/2000 |
| WO | 0011000 | 6/2000 |
| WO | 0050011 | 8/2000 |
| WO | 0035428 | 9/2000 |
| WO | 0051598 | 9/2000 |
| WO | 0053182 | 9/2000 |
| WO | 0063211 | 10/2000 |
| WO | 0066123 | 11/2000 |
| WO | 0074654 | 12/2000 |
| WO | 0108686 | 2/2001 |
| WO | 0115678 | 3/2001 |
| WO | 0132165 | 5/2001 |
| WO | 0146136 | 6/2001 |
| WO | 0157025 | 8/2001 |
| WO | 0160358 | 8/2001 |
| WO | 0190076 | 11/2001 |
| WO | 0209689 | 2/2002 |
| WO | 0238155 | 5/2002 |
| WO | 02/45693 A1 | 6/2002 |
| WO | 02/072072 A2 | 9/2002 |
| WO | 03039552 | 5/2003 |
| WO | 03/070279 A1 | 8/2003 |
| WO | 03002593 | 8/2003 |
| WO | 03097050 | 11/2003 |
| WO | 03099278 | 12/2003 |
| WO | 03099334 | 12/2003 |
| WO | 03105902 | 12/2003 |
| WO | 2004017974 | 3/2004 |
| WO | 2004019944 | 3/2004 |
| WO | 2004033430 | 4/2004 |
| WO | 2004/052345 A1 | 6/2004 |
| WO | 2004/066974 A1 | 8/2004 |
| WO | 2004080967 | 9/2004 |
| WO | 2004103407 | 12/2004 |
| WO | 2005/013944 A1 | 2/2005 |
| WO | 2005011602 | 2/2005 |
| WO | 2005/020961 A1 | 3/2005 |
| WO | 2005026095 | 3/2005 |
| WO | 2005034871 | 4/2005 |
| WO | 2005041864 | 5/2005 |
| WO | 2006097456 | 9/2006 |
| WO | 2008006050 | 1/2008 |

OTHER PUBLICATIONS

Barsig et al., "The Novel Phosphodiesterase-4 Inhibitor Roflumilast Suppresses TNF-a Production and in Combination with Methotrexate Efficiently Protects Mice Against Collagen-induced Arthritis," Arthritis and Rheumatic Diseases, 2001, Poster Presentation, 1 page.

Barsig et al., "The Novel Phosphodiesterase-4 Inhibitor Roflumilast Suppresses TNF-a Production and Efficiently Protects Mice Against Collagen-Induced Arthritis Alone and in Combination with Methotrexate", *Arthritis and Rheumatic Diseases,* 2001, 44(9):Suppl. S367, Abstract.

Bateman et al., "Efficacy of roflumilast in patients with a history of frequent exacerbations: pooled data from pivotal 12-month studies," Poster, ERS Barcelona, Sep. 2010, 1 page.

Barnes, "Emerging pharmacotherapies for COPD," *Chest,* 2008, 134:1278-86.

Bauer et al., "Lehrbuch der Pharmazeutischen Technologie," 2003, p. 56.

Beers, Merck Manual of Diagnosis and Therapy 17th Edition, 1999, pp. 568-569,XP002300786.

Bethke et al., "Smoking Has No Effect on the Pharmacokinetics of Roflumilast—a New, Orally Active, Selective PDE4 Inhibitor," *Eur Respir J.,* 2001, Poster Presentation, 1 page.

Bethke et al., "Roflumilast, a New, Orally Active, Selective PDE4 Inhibitor, Does Not Interact with Inhaled Budesonide", *Eur Respir J,* 2001, Poster Presentation, 1 page.

Bundschuh et al., "In vivo eficacy in airway disease models of roflumilast, a novel orally active PDE4 inhibitory," J. Pharmacol. Exp. Thera., 2000, 297(1):280-290.

Calverley et al., "Effect of roflumilast on lung function," ATS 2006 Presentation, 12 pages.

Calverly, P., Lancet 2003, vol. 361, pp. 449-456.

Calverley et al., "Roflumilast in symptomatic chronic obstructive pulmonary disease: two randomized clinical trials," *Lancet,* 2009, 374: 685-94, Supplementary Web Appendix Content.

Casas J P J Intern Med 2008 vol. 264 p. 295-314.

Celli and MacNee, "Standards for the diagnosis and treatment of patients with COPD: A summary of the ATS/ERS position paper," *Eur Respir J,* 2004, 23:932-46.

Chen at al., "Long-acting bronchodilator therapy for the treatment of chronic obstructive pulmonary disease," *Ann Pharmacother,* 2008, 42:1832-42.

Chiou and Riegelman, "Pharmaceutical applications of solid dispersion systems," *J. Pharm. Sci.,* 1971, 60:1281-1302.

Chinese Office Action in CN application No. 03804230.4, dated Mar. 29, 2009, 11 pages.

Cocci et al., "Urinary desmosine excretion is inversely correlated with the extent of emphysema in patients with chronic obstructive pulmonary disease," *Int J Biochem Cell Biol,* 2002, 36(6):594-604.

Cook et al., "Process Development o the PDE IV Inhibitor 3-(Cyclopentyloxy)-*N*-(3,5-dichloropyrid-4-yl)-4-methoxybenzamide," *Organic Process Research & Development,* 1998, 2:157-168.

David et al., "Influence of Food Intake on the Pharmacokinetics of Roflumilast, a New, Orally Active, Selective PDE4 Inhibitor", *Eur Respir J,* 2001, Poster Presentation, 1 page.

David et al., "Influence of food intake on the pharmacokinetics of roflumilast, a new, orally active, selective PDE4 inhibitor", *Eur Respir J,* 2001, 18:Suppl. 33, 42s, Abstract.

Declaration of Dirk Bredenbroeker under Rule 1.132 dated Aug. 17, 2012 in U.S. Appl. No. 11/501,836, filed Aug. 10, 2006, 7 pages.

Declaration of Hermann Tenor under Rule 1.132 dated Aug. 16, 2012 in U.S. Appl. No. 11/501,836, filed Aug. 10, 2006, 9 pages.

Declaration of Hermann Tenor under Rule 1.132 date Nov. 9, 2012 in U.S. Appl. No. 12/876,996, filed Sep. 7, 2010, 3 pages.

(56) References Cited

OTHER PUBLICATIONS

Declaration of Hartmut Ney under Rule 1.132 dated Apr. 19, 2007 in U.S. Appl. No. 10/505,138, filed Aug. 19, 2004, 25 pages.
Declaration of Walter Palosch under Rule 1.132 dated Mar. 13, 2013 in U.S. Appl. No. 13/547,945, filed Jul. 12, 2012, 4 pages.
Declaration of Karl Zech under Rule 1.132 dated Jan. 24, 2013 in U.S. Appl. No. 12/876,996, filed Sep. 7, 2010, 4 pages.
Definition: "Solution, colloidal," In: Hawleys Chemical Condensed Dictionary, 14th edition, 2002, 1 page.
Drugs in R and D-ADIS R&D Profile ,"Roflumilast," 2004, 5(3):176-181, XP008036613.
deMey et al., "Repeated-dose Co-administration of Roflumilast and Formoterol Does not Alter the Pharmacokinetics of Either Drug," ATS 2006 Poster, 2006, 1 page.
deMey et al., "Roflumilast Does not Potentiate Tachycardia Associated with Formoterol," ATS 2006 Poster, 2006, 1 page.
Donaldson G C Thorax 2002 vol. 57 p. 847-52.
Eakin et al., "Validation of a new dyspnea measure: The UCSD shortness of breath questionnaire," Chest, 1998, 113:619-24.
Ecuador Office Action in EC application No. SP-045238, dated Jul. 31, 2008, 3 pages.
Engelstatter, "Roflumilast, an oral, once-daily phosphodiesterase 4 (PDE4) inhibitor, does not exhibit bronchodilatory activity," *Ann Allergy Asthma Immunol*, 2005, 94:169 (Abstract).
Europe Office Action in EP application No. 03704652.1, dated Nov. 19, 2010, in corresponding EP case citing EP1161950A1, 6 pages.
Exhibit B-5 Handbook of Pharmaceutical Excipients, 2nd Ed, Wade and Weller Eds., 1994, 4 pages.
Exhibit B-6 Release controlled Oral Preparation, 3 pages, Sep. 2002.
Fabbri L M Lancet 2009 vol. 374 p. 695-703.
Fabbri L M Lancet 2009 vol. 374 p. 695-703; Webappendix.
Fabbri et al, "Effect of Roflumilast on Exacerbations: a 1-year Study in Patients with Severe to Very Severe COPD ," ATS 2006 Poster, 2006, 1 page.
Facius et al., "Modelling and simulation based techniques to support trial design of roflumilast phase III trials," 2011, Athens Jun. 7-10, 2011, Poster, Modelling Simulation techniques Trial Design, Roflumilast, 1 page.
FDA PADAC Roflumilast, Questions and Answers presented UCM20871207, Apr. 2010, 27 pages.
Fialkov, *Chemical Abstracts*, 1983, 98(23):603.
Fox,"Efficacy of the PDE4 inhibitor, BAY 19-8004, in tobacco smoke models of COPD in the guinea pig," *Am J Resp Crit Care Med*, 2003, 167:A91.
German, "Reliability of drop size from multi-dose eye drop bottles: is it cause for concern?," *Pub Med Resul*, 1999, 13:93-100.
Griswold, "SB 207499 (Ariflo), a second generation phosphodiesterase 4 inhibitor, reduces tumor necrosis factor alpha and interleukin-4 production in vivo," *J. Pharm. and Exper. Therap.*, 1998, 287(2):705-711.
Grootendorst D C Thorax 2007 vol. 62 p. 1081-87.
Grootendorst et al., "Does a single dose of the phosphodiesterase 4 inhibitor, cilomilast (15 mg), induce bronchodilation in patients with chronic obstructive pulmonary disease?," *Pulmonary_Pharmacology_and_Therapeutics*, 2003, 16:115-120.
"Guidance for Industry, Chronic Obstructive Pulmonary Disease: Developing Drugs for Treatment," 2007, 17 pages.
Hafner et al., "Additive Effects of Phosphodiesterase-4 Inhibition on Effects of rSP-C Surfactant", *AmJ Respir Crit Care Med*, 2000, 161:1495-1500.
Hahn, *Chemical Abstracts*, 1963, 58(9):8943-8944.
Hanifin, "Type 4 Phosphodiesterase inhibitors have clinical and in vitro anti-inflammatory effects in atopic dermatitis," *J Journal of Investigative Dermatology*, 1996, 107:51-56.
Hatzelmann et al., Anti-Inflammatory and immunomodulatory potential of the novel PDE4 inhibitor roflumilast in vitro, J. Pharm. Exp. Thera., 2000, 297(1):267-279.
Hauns et al., "Four-week treatment with the new PDE4 inhibitor roflumilast in patients with exercise-induced asthma: safety, efficacy and inhibition of TNF-a ex vivo," *Eur Respir J*, 2000, 16:Suppl. 31, A3805, Abstract.
Hauns et al., "Safety-related performance is not impaired by the new PDE-4 inhibitor Roflumilast", *Eur Respir J*, 2000, 16:Suppl. 31, 277S, Abstract.
Herberg et al., "Treatment with the New PDE4 Inhibitor Roflumilast Does Not Impair Vigilance and Traffic Safety", *Eur J Clin Pharmacol*, 2000, 56(2), A29, Abstract.
Hermann R J Clin Pharmacol 2007 vol. 47 p. 1005-1013.
Hilden, "Physics of amorphous solids," *J of Pharma Sciences*, 2004, 93:3-12.
Hoymann et al., "Inhibition by Roflumilast of Airway Hyper-responsiveness to Acetylcholine 48 h after Allergen Challenge in Rats", *Am J Respir Crit Care Med*, 2001, Poster Presentation, 1 page.
Hoymann et al., "Inhibition by Roflumilast of Airway Hyper-responsiveness to Acetylcholine 48H After Allergen Challenge in Rats", *Am J Respir Crit Care Med*, 2001, 163:A431, Abstract.
Hunnemeyer et al., "Pharmacokinetics of Roflumilast and its Active Metabolite Roflumilast-N-Oxide Is Not Influenced by Smoking", *Am J Respir Crit Care Med*, 2002, Poster Presentation, 1 page.
Hunnemeyer al., "Pharmacokinetics of Roftumilast and its Active Metabolite, Roflumilast-N-Oxide, Is Not Influenced by Smoking", *Am J Respir Crit Care Med*, 2002, 165:A594, Abstract.
Izikki et al., "Effects of Roflumilast, a Phosphodiesterase-4 Inhibitor, on Hypoxia- and Monocrotaline-Induced Pulmonary Hypertension in Rats", *The Journal of Pharmacology and Experimental Therapeutics*, 2009, 330, 1:54-62, The American Society for Pharmacology and Experimental Therapeutics.
Japanese Office Action in JP application No. 2003-569234, dated Sep. 14, 2007, 17 pages.
Kast, "Chapter 1: Ointment," *Pharmaceutics*, 1998, 25 pages.
Kazumasa., "Preparation of N-pyridyl-4-(benzyloxy) benzamides as cardiotonics," *Chemical Abstracts*, 1988, 108(15):Abstract No.__ 131583p.
Keene et al., "Statistical analysis of COPD exacerbations," *Eur Respir J*, 2008, 32:1421-1422.
Keene et al., "Statistical analysis of exacerbation rates in COPD: Tristan and Isolde revisited," *Eur Respir J*, 2008, 32:17-24.
Keipert et al., "Wechselwirkungen zwischen makromolekularen hilfsstoffen und arzneistoffen," *Pharmazie*, 1986, 41:400-404.
Kessler R Chest 2006 vol. 130 p. 133-42.
Korean Office Action in KR application No. 10-2004-7012904, dated Oct. 7, 2010, 14 pages.
Kumar Rakesh K J Pharmacol Exp Ther 2003 vol. 307 p. 349-355.
Kurashima et al., "A pilot study of surfactant inhalation for the treatment of asthmatic attack," *Jpn J Allergol*, 1991, 40:160-163.
Lahu et al., "Effects of steady-state enoxacin on single-dose pharmacokinetics of roflumilast and roflumilast N-oxide," ERS Sep. 2009 Poster, 2009, 1 page.
Lahu et al., "Modeling and simulation in successful drug development Programs: characterization of exacerbation reduction with roflumilast to corroborate the importance of defining patient subsets in COPD," ERS Sep. 2011 Modelling Simulation, 2011, 1 page.
Lahu G J Clin Pharm 2010.
Lanes S F Am J Respir Crit Care Med 2008 vol. 178 p. 543-44.
Leichtl et al., "Efficacy of Once-Daily Roflumilast, a New, Orally Active Selective Phosphodiesterase 4 Inhibitor, in Chronic Obstructive Pulmonary Disease", *Am J Respir Crit Car Med*, May 2002, 165:A229.
Leichtl et al., "Efficacy of Once-Daily Roflumilast, A New, Orally Active, Selective Phosphodiesterase 4 Inhibitor, in Chronic Obstructive Pulmonary Disease," May 2002, poster, 1 page.
Lewis et al., "The physical and chemical stability of suspensions of sustained-release diclofenac microspheres," *Microencapsulation*, 1998, 15:5-567 XP000771706.
Lipworth, "Phosphodiesterase-4 inhibitors for asthma and chronic obstructive pulmonary disease," *Lancet*, 2005, 365:167-175.
Macintyre, "Chronic obstructive pulmonary disease," *Pharmacotherapy*, 2004, 24(5):33S-43S XP008036609.
Mahler D A Chest 1984 vol. 85 p. 751-58.

(56) References Cited

OTHER PUBLICATIONS

Martin, "PDE4 inhibitors—A review of the recent patent literature," *IDrugs,* 2001, 4(3):312-338, PharmaPress LId.
Meyer, "Charackterisierung und Beeinflussung der Losungseigenschaften von 6-Bromcip", Dissertation 1995, 1995, pp. 154-189.
Mueller, *Pharmazeutische Technologie Moderne Arzneiformen,* 1997, pp. 80-91.
Muise et al., "Comparison of inhibition of ovalbumin-induced bronchoconstriction in guinea pigs and in vitro inhibition of tumor necrosis factor-a formation with phosphodiesterase 4 (PDE4) selective inhibitors," *Biochem Pharmacol,* 2002, 63:1527-35.
Nassr et al., "Effects of CYP3A4 by Rifampicin on the Pharmacokinetics of roflumilast and roflumilast N-oxide," German pharmacology Meeting, Wurzburg, 2006, Poster, Rifampicin Roflumilast, 1 page.
Nell et al., "Acute Anti-Inflammatory Effect of the Novel Phosphodiesterase 4 Inhibitor Roflumilast on Allergen Challenge in Asthmatics After a Single Dose", *Am J Respir Crit Care Med,* 2000, 161(3):Part 2, A200, Abstract.
Norman, "PDE4 inhibitors 1999," *Expert Opinion Therapeutic Patents,* 1999, 9(8):1101-1118.
Odian, *Principles of polymerization,* Wiley Sons, 1991, pp. 19-23.
O'Donnell et al., "Canadian thoracic society recommendations for management of chronic obstructive pulmonary disease—2008 update—highlights for primary care," *Can Respir J,* 2008, 15:Suppl A P, pp. 1A-8A.
Office Action PH Jun. 16, 2009.
Opposition filed in the name of Hexal AG against EP1478399 of Nycomed GmbH, filed Feb. 20, 2003, granted Mar. 21, 2012, 8 pages.
Pfizer Centre Source, "Dexamethasone USP Micronized," 2010, 5 pages.
Pharmacy ,4th ed., pp. 114-117 Dec. 2000,The Peoples Medical Publishing House, edited by BI Dianzhou.
Pleiss et al., "Synthesis of [18F] Labelled Roflumilast using difluoro [18F] bromomethane as alkylating agent," *Synth. Appl. Isotop. Lab. Comp.,* 2000, 7:375-376.
Poppe et al., "Effects of a Selective PDE4-Inhibitor AWD 12-281 in Comparison With SB 207499 and Roflumilast on Tracheal Phenol Red Secretion in Mice and LPS-Induced Neutrophilia in BAL in Lewis Rats and Domestic Pigs", *Am J Respir Crit Care Med,* 2001, 163(5): A, Abstract.
Pruniaux, "Efficacy of a selective phosphodiesterase 4 inhibitor, CI-1044, on cigarette smoke-induced emphysema development in mice," *Am J Resp Crit Care Med,* 2003, 167:A874.
PVP disclosure—downloaded from the internet, Jan. 21, 2008, 2 pages.
Quanjer et al., "Lung volumes and forced ventilatory flows," *Eur Respir J,* 1993, 6(suppl): 5-40.
Rabe et al., "Theophylline and selective PDE inhibitors as bronchodilators and smooth muscle relaxants," *Eur Respir J,* 1995, 8 :637-42.
Rabe K F A J Respir Crit Care Med 2007 vol. 176 p. 532-55.
Rabe K F Expert Reviews Resp Med 2010 vol. 4 p. 543-555.
Rabe K F Lancet 2005 vol. 366 p. 563-71.
Rabe Lancet 2005 vol. 366 p. 1846-1847.
Rabin R Ann Med 2001 vol. 33 p. 337-43.
Reid, "Roflumilast," *Current Opinion in Investigational Drugs,* 2002, 3(8):1165-1170 XP001119630.
Reid, "Cytokines in the pathogenesis of chronic obstructive pulmonary disease," *Current Pharmaceutical Design,* 2003, 9:25-38 XP008036607.
Rennard_S Respiratory Research 2011 vol. 18 p. 12.
Response to Official Action and data filed Nov. 9, 2009 in corresponding European Patent Application No. 03704652.1-2123, 27 pages.
Roflumilast—European Approval Documents Daxas, Package Leaflet.
Roflumilast—European Approval Documents Daxas, "Summary of Product Characteristics," Annex 1, 2010, 11 pages.
Roflumilast—Daliresp Full Prescribing Information, FDA, 2011, 14 pages.
Rolando, *Survey of Ophthalmology,* 2001,45:S203-S210.
Safety data sheet Crodesta F10-HB03671 Sucrose Distearate Croda Europe Ltd, 2005, 1 page.
Safety data sheet Crodesta F110 HB03722Sucrose Stearate and Sucrose Stearate Croda Europe Ltd, 2005, 1 page.
Safety data sheet Crodesta F160 HB03750 Sucrose Stearate Croda Europe Ltd, 2005, 1 page.
Safety data sheet Crodesta F20 HB03668 Sucrose Distearate Croda Europe Ltd, 2005, 1 page.
Safety data sheet Crodesta F50 HB03669 Sucrose Distearate Croda Europe Ltd, 2005, 1 page.
Safety data sheet Crodesta SL40 HB03791 Aqua and Sucrose Cocoate and Alcohol Croda Europe Ltd, 2005, 1 page.
Schmidt., "The phosphodiesterase 4 inhibitor roflumilast is effective in the treatment of allergic rhinitis," *J Allergy Clin Immunol,* 2001, 108(4):30-536, Mosby, Inc.
Sin D D Thorax 2006 vol. 61 p. 1-3.
Sin and Man, "Systematic inflammation and mortality in chronic obstructive pulmonary disease," *Can J Phsiol Pharmacol* ,2007, 85:141-47.
Singh et al., "Long-term use of inhaled-corticosteroids and the risk of pneumonia in chronic obstructive pulmonary disease," *Arch Intern Med,* 2009, 169: 219-229.
Snoeck-Stroband J B Eur Respir J 2008 vol. 31 p. 70-77.
Soler-Cataluna JJ Thorax 2005 vol. 60 p. 925-31.
Solutol HS 15 Technical Information, BASF, Jul. 2003, 8 pages.
Sorbera., "Roflumilast: Antiallergy/Antiasthmatic Treatment of COPD Phosphodiesterase 4 Inhibitor", *Drugs of the Future,* 2000, 25(12):1261-1264, Prous Science.
Spencer S Am J Respir Crit Care Med 2001 vol. 163 p. 122-128.
Spina D Br J Pharmacol 2008 vol. 155 p. 308-15.
Stebbins et al., "Aerosol activity of phosphodiesterase type IV inhibitors in a murine model of cigarette smoke induced pulmonary inflammation," Am J Resp Crit Care Med, 2003, 167:A486.
Stockley R A Thorax 2006 vol. 61 p. 122-28.
Strickley, "Solubilizing excipients in oral and injectable formulations," *Pharmaceutical Research,* 2004, 212:201-230.
Sucker et al., Pharmazeutische Technologie: Beschrelbung der Arznelformen Spezielle Entwicklung der Dermatika, 1978, p. 629-636 and p. 650-665.
Suissa et al., "Passive smoking and asthma death," *Eur Respir J,*2008, 32:1117-18.
Szafranski et al., "Efficacy and safety of budesonide/formoterol in the management of chronic obstructive pulmonary disease," *Eur Respir J,* 2003, 21: 74-81.
Tashkin D P N Engl J Med 2008 vol. 359 p. 1543-54.
Tenor et al, "Pharmacology, Clinical Efficacy, and Tolerability of Phosphodiesterase-4 Inhibitors: Impact of Human Pharmacokinetics", Handbook of Experimental Pharmacology, 2011, pp. 85-119.
Thurlbeck, *American Review Respiratory Disease,* 1967, 95(5):752-764 XP008036612.
Timmer et al, "Safety and Efficacy of the New PDE4 Inhibitor Roflumilast Administered to Patients with Exercise-Induced Asthma Over 4 Weeks", *Am J Respir Crit Care Med,* 2000, 161(3):Part 2, A505, Abstract.
Timmer et al., "The Clinical Efficacy of the New PDE4 Inhibitor Roflumilast in Exercise-Induced Asthma is Accompanied by Suppression of LPS-Stimulated TNF-a Levels", *Europ J Clin Pharm,* 2000, 56(2):A29, Abstract.
Timmer et al., "Treatment with Therapeutic Doses of the New PDE4 Inhibitor Roflumilast Does Not Influence Cardiovascular Function", *Europ J Clin Pharm,* 2000, 56(2):A29, Abstract.
Toshiro et al., "Yakuzai-gaku" (Pharmaceutics), issued by Konando, 1997, 5th edition, pp. 112 to 114 (with English translation).
Tros de Ilarduya et al., "Solubilization and Interaction of Sulindac with Polyvinylpyrrolidone K30 in the Solid State and in Aqueous Solution", *Drug Development and Industrial Pharmacy,* 1998, 24(3):295-300.
Von Richter O Clin Pharmacokin 2007 vol. 46 p. 613-622.
Washington, "Ocular drug delivery," *Ocular drug delivery particulates,* 2000, pp. 265, 16 pages.

(56) References Cited

OTHER PUBLICATIONS

Wedzicha et al., "The prevention of chronic obstructive pulmonary disease exacerbations by salmeterol/fluticasone propionate or tiotropium bromide," *Am J Respir Crit Care Med*, 2008, 177: 19-26.
Weimar et al., "No Interaction of Roflumilast, a New, Orally Active, Selective PDE4 Inhibitor, with Inhaled Salbutamol", *Eur Respir J*, 2001, Poster Presentation, 1 page.
Weimar et al., "No interaction of roflumilast, a new, orally active, selective PDE4 inhibitor, with inhaled salbutamol", *Eur Respir J*, 2001, vol. 18, Suppl. 33, 156s, Abstract.
Wollin et al., "Inhibition by Roflumilast of Airway Hyperresponsiveness to Adenosine and Pulmonary Inflammation in Allergen-challenged Brown Norway Rats", *Eur Respir J*, 2001, Poster Presentation, 1 page.
Wollin et al., "Inhibition by Roflumilast of Airway Hyperresponsiveness to Adenosine and Pulmonary Neutrophil Accumulation 3H After Allergen Challenge in Rats", *Am J Respir Crit Care Med*, 2001, 63:A432, Abstract.
Wollin et al., "Inhibition by roflumilast of airway hyperresponsiveness to adenosine and pulmonary inflammation in allergen challenged Brown-Norway rats", *Eur Respir J*, 2001,18:Suppl. 33, 35s, Abstract.
Yagupolskii, *Chemical Abstracts*, 1961, 55:18.
Yliruusi et al., "A new Method to evaluate the elastic behavior of tablets during compression," *Drug: Oev. Ind. Pharm.*, 1997, 23(1):63-68.
Zech et al., "High oral bioavailabiity of roflumilast, a new, orally active once daily PDE4 inhibitor," *Eur Respir J*, 2001, 11 pages.
Zech et al., "High oral absolute bioavailability of roflumilast, a new, orally active, once daily PDE4 inhibitor", *Eur Respir J*, 2001, 18:Suppl. 33, 20s, Abstract.
Zelko et al., "Effects of storage conditions on the free volume of polyvinylpyrrolidone: comparison of positron lifetime data with tensile strength of tablet", *Pharm. Res.*, 2000, 17(8):1030-1032.
ZuWallack et al., "Salmeterol plus theophylline combination therapy in the treatment of COPD," Chest, 2001, 119: 1661-70.
Applicant Appeal Briefs filed in U.S. Appl. No. 10/515,698, filed Aug. 26, 2009 and Oct. 26, 2009, 36 pages.
Applicant Appeal Brief filed in U.S. Appl. No. 12/149,250, filed Mar. 21, 2011, 20 pages.
Applicant Appeal Brief filed in U.S. Appl. No. 10/515,896, filed Jan. 26, 2011, 37 pages.
Applicant Appeal Brief filed in U.S. Appl. No. 11/662,887, filed Feb. 2, 2012, 33 pages.
Applicant Appeal Brief filed in U.S. Appl. No. 10/505,138, filed Mar. 30, 2009, 40 pages.
Applicant Reply Brief filed in U.S. Appl. No. 10/515,896, dated Jun. 13, 2011, 26 pages.
Applicant Reply Brief filed in U.S. Appl. No. 11/662,887, filed May 30, 2012, 13 pages.
Applicant Reply Brief filed in U.S. Appl. No. 10/515,698, filed Mar. 29, 2010, 12 pages.
Applicant Reply Brief filed in U.S. Appl. No. 10/505,138, filed Aug. 3, 2009, 37 pages.
USPTO Non-final Office Action issued in U.S. Appl. No. 12/149,250, dated Apr. 20, 2010, 13 pages.
USPTO Final Office Action issued in U.S. Appl. No. 12/149,250, dated Oct. 27, 2010, 8 pages.
USPTO Non-final Office Action issued in U.S. Appl. No. 10/515,698, dated Jan. 23, 2008, 14 pages.
USPTO Restriction Requirement issued in U.S. Appl. No. 10/515,896, dated Mar. 13, 2009, 6 pages.
USPTO Final Office Action issued in U.S. Appl. No. 10/515,896, dated Mar. 26, 2010, 20 pages.
USPTO Restriction Requirement issued in U.S. Appl. No. 10/515,698, dated Oct. 9, 2007, 9 pages.
USPTO Final Office Action issued in U.S. Appl. No. 10/505,138, dated Feb. 2, 2006, 10 pages.
USPTO Final Office Action issued in U.S. Appl. No. 10/505,138, dated May 30, 2007, 7 pages.
USPTO Final Office Action issued in U.S. Appl. No. 10/505,138, dated Oct. 16, 2008, 8 pages.
USPTO Final Office Action issued in U.S. Appl. No. 10/505,138, dated Nov. 12, 2008, 8 pages.
USPTO Final Office Action issued in U.S. Appl. No. 11/501,836, dated May 7, 2010, 13 pages.
USPTO Final Office Action issued in U.S. Appl. No. 11/501,836, dated Oct. 11, 2012, 73 pages.
USPTO Final Office Action issued in U.S. Appl. No. 12/876,996, dated Oct. 11, 2012, 58 pages.
USPTO Non-final Office Action issued in U.S. Appl. No. 10/505,138, dated Sep. 1, 2005, 9 pages.
USPTO Non-final Office Action issued in U.S. Appl. No. 10/505,138, dated Nov. 3, 2006, 16 pages.
USPTO Non-final Office Action issued in U.S. Appl. No. 10/505,138, dated Feb. 27, 2008, 15 pages.
USPTO Patent Board Decision issued in U.S. Appl. No. 10/505,138, dated Oct. 20, 2010, 19 pages.
USPTO Examiner's Answer to Appeal Brief issued in U.S. Appl. No. 10/505,138, dated Jun. 2, 2009, 19 pages.
USPTO Non-final Office Action issued in U.S. Appl. No. 10/531,720, dated Jan. 18, 2008, 7 pages.
USPTO Non-final Office Action issued in U.S. Appl. No. 12/292,795, dated Aug. 11, 2011, 10 pages.
USPTO Notice of Allowance issued in U.S. Appl. No. 10/505,138, dated Mar. 18, 2011, 55 pages.
USPTO Notice of Allowance issued in U.S. Appl. No. 13/008,842, dated Oct. 15, 2012, 44 pages.
USPTO Notice of Allowance issued in U.S. Appl. No. 13/008,842, dated Dec. 18, 2012, 4 pages.
USPTO Notice of Allowance issued in U.S. Appl. No. 13/008,842, dated Feb. 27, 2013, 12 pages.
USPTO Notice of Allowance issued in U.S. Appl. No. 13/008,842, dated Jan. 28, 2013, 5 pages.
USPTO Notice of Allowance issued in U.S. Appl. No. 10/531,720, dated Aug. 28, 2008, 6 pages.
USPTO Notice of Allowance issued in U.S. Appl. No. 12/292,795, dated Apr. 24, 2012, 7 pages.
USPTO Suppl Notice of Allowability issued in U.S. Appl. No. 10/531,720, dated Nov. 7, 2008, 4 pages.
USPTO Restriction Requirement issued in U.S. Appl. No. 11/642,621, dated May 15, 2009, 9 pages.
USPTO Non-final Office Action issued in U.S. Appl. No. 11/642,621, dated May 19, 2010, 14 pages.
USPTO Final Office Action issued in U.S. Appl. No. 11/642,621, dated Nov. 1, 2010, 8 pages.
USPTO Notice of Allowance issued in U.S. Appl. No. 11/642,621, dated Jan. 24, 2011, 6 pages.
USPTO Final Office Action issued in U.S. Appl. No, 10/515,698, dated Aug. 19, 2008, 9 pages.
USPTO Non-final Office Action issued in U.S. Appl. No. 10/433,398, dated Jan. 11, 2006, 14 pages.
USPTO Final Office Action issued in U.S. Appl. No. 10/433,398, dated Jul. 3, 2006, 9 pages.
USPTO Notice of Allowance issued in U.S. Appl. No. 10/433,398, dated Sep. 21, 2006, 5 pages.
USPTO Final Office Action issued in U.S. Appl. No. 10/515,698, dated Jan. 16, 2009, 7 pages.
USPTO Examiner's Answer to Appeal Brief issued in U.S. Appl. No. 10/515,698, dated Feb. 2, 2010, 11 pages.
USPTO Patent Board Decision issued in U.S. Appl. No. 10/515,698, dated Jun. 27, 2011, 8 pages.
USPTO Non-final Office Action issued in U.S. Appl. No. 13/219,056, dated Oct. 19, 2011, 18 pages.
USPTO Final Office Action issued in U.S. Appl. No. 13/219,056, dated Apr. 25, 2012, 10 pages.
USPTO Examiner's Answer to Appeal Brief issued in U.S. Appl. No. 12/149,250, dated Jun. 8, 2011, 10 pages.
USPTO Non-final Office Action issued in U.S. Appl. No. 10/515,896, dated Jun. 23, 2009, 17 pages.
USPTO Non-final Office Action issued in U.S. Appl. No. 10/515,896, dated Sep. 14, 2010, 26 pages.

(56) References Cited

OTHER PUBLICATIONS

USPTO Examiner's Answer to Appeal Brief issued in U.S. Appl. No. 10/515,896, dated Apr. 14, 2011, 31 pages.
USPTO Patent Board Decision issued in U.S. Appl. No. 10/515,896, dated Jun. 13, 2013, 18 pages.
USPTO Non-final Office Action issued in U.S. Appl. No. 11/662,887, dated Jun. 28, 2010, 18 pages.
USPTO Non-final Office Action issued in U.S. Appl. No. 11/662,887, dated Dec. 16, 2010, 16 pages.
USPTO Final Office Action issued in U.S. Appl. No. 11/662,887, dated Jun. 8, 2011, 12 pages.
USPTO Examiner's Answer to Appeal Brief issued in U.S. Appl. No. 11/662,887, dated Mar. 30, 2012, 19 pages.
USPTO Restriction Requirement issued in U.S. Appl. No. 11/662,888, dated Sep. 15, 2008, 8 pages.
USPTO Non-Final Office Action issued in U.S. Appl. No. 11/501,836, dated Aug. 7, 2009, 12 pages.
USPTO Non-Final Office Action issued in U.S. Appl. No. 12/876,996, dated Feb. 29, 2012, 14 pages.
USPTO Non-Final Office Action issued in U.S. Appl. No. 13/008,842, dated Jan. 4, 2012, 11 pages.
USPTO Non-Final Office Action issued in U.S. Appl. No. 11/501,836, dated Mar. 20, 2009, 7 pages.
USPTO Non-Final Office Action issued in U.S. Appl. No. 11/501,836, dated Feb. 29, 2012, 9 pages.
USPTO Notice of Allowance issued in U.S. Appl. No. 13/547,945, dated May 2, 2013, 40 pages.
USPTO Non-Final Office Action issued in U.S. Appl. No. 13/860,264, dated Jun. 12, 2013, 31 pages.
USPTO Non-Final Office Action issued in U.S. Appl. No. 13/860,248, dated Jun. 12, 2013, 29 pages.
USPTO Notice of Allowance issued in U.S. Appl. No. 13/547,945, dated Jul. 22, 2013, 13 pages.
USPTO Non-Final Office Action issued in U.S. Appl. No. 11/885,837, dated Sep. 14, 2010, 13 pages.
USPTO Non-Final Office Action issued in U.S. Appl. No. 11/885,837, dated May 23, 2013, 9 pages.
Bethke et al., "Roflumilast, a new, orally active, selective PDE4 inhibitor, does not interact with inhaled budesonide", *Eur Respir J*, 2001, 18:Suppl. 33, 156s, Abstract.
Bethke et al., "Smoking has no effect on the pharmacokinetics of roflumilast, a new, orally active, selective PDE4 inhibitor", *Eur Respir J*, 2001, 18:Suppl. 33, 156s, Abstract.
Bethke et al., "The New PDE4 Inhibitor Roflumilast Does Not Influence Cardiovascular Function", *Am J Respir Crit Care Med*, 2001, 163:A431, Abstract.
Boehmer et al., "Effects of the Dual Pathway Inhibitor Cimetidine on the Pharmacokinetics of Roflumilast and Roflumilast N-oxide," VKliPha 2007 Poster, 2007, 1 page.
Boswell et al., "Are phosphodiesterase 4 inhibitors just more theophylline?," *J. Allergy Clin. Immunol.*, 2006, 117:1237-43.
Bredenbroker et al., "Safety of Once-Daily Roflumilast, a New, Orally Active, Selective Phosphodiesterase 4 Inhibitor, in Patients with COPD," May 2002, poster, 1 page.
Bredenbroker et al., "Safety of Once-Daily Roflumilast, a New, Orally Active, Selective Phosphodiesterase 4 Inhibitor, in Patients with COPD", *Am J Respir Crit Care Med*, May 2002, 165, A595.
Brusasco v Thorax 2003 vol. 58, p. 399-404.
Buehler, "Kollidon: Polyvinylpyrrolidone for the pharmaceutical industry", 2th Ed., BASF, 1995, pp. 1-287.
Buehler, Kollidon: Polyvinylpyrrolidone for the pharmaceutical industry, 4th ed., BASF, 1998, 14 pages, Kollidone Handbook.
Bundschuh et al., "Antiinflammatory and Immunomodulatory Potential of Roflumilast, a Novel PDE4 Inhibitor", *Am J Respir Crit Care Med*, 2001, vol. 163, A431, Abstract.
Bundschuh et al., "In vitro and in vivo anti-inflammatory activity of the novel PDE4 inhibitor roflumilast", *Eur Respir J*, 2001, 18:Suppl. 33, 35s, Abstract.
Bundschuh et al.. "In Vitro and in Vivo Anti-Inflammatory Activity of the Novel PDE4 Inhibitor Roflumilast," *Eur Respir J.*, 2001, Poster Presentation, 1 page.
Bundschuh et al., "In vivo efficacy in airway disease models of roflumilast, a novel orally active PDE4 inhibitory," J. Pharmacol. Exp. Thera., 2000, 297(1):280-290.
Burge et al., "Randomized, double blind, placebo controlled study of fluticasone propionate in patients with moderate to severe chronic obstructive pulmonary disease: the ISOLDE trial," *BMJ*, 2000, 320:1297-1303.
Calverley et al., "Defining patient populations in COPD: experience with roflumilast," COPD7 Birmingham, 2010, 1 page.
Calverly P M A Lancet 2009 vol. 374 p. 685-94.
Calverly P M Am J Respir Crit Care Med 2007 vol. 176 p. 154-61.
Calverly P M Eur Respir J 2003 vol. 22 p. 912-19.
Calverly P M Lancet 2003 vol. 362 p. 1053-61.
Calverly P M N Engl J Med 2007 vol. 356 p. 775-89.
Calverly P M Respir Res 2008 vol. 9 p. 73.

* cited by examiner

TASTE MASKED DOSAGE FORM CONTAINING ROFLUMILAST

This application was filed under 35 U.S.C. 371 as a national stage of PCT/EP2006/060679, filed Mar. 14, 2006.

TECHNICAL FIELD

The present invention relates to the field of pharmaceutical technology and describes taste masked particles and dosage forms for oral administration of roflumilast as active ingredient for treating diseases such as asthma or airway obstructions. The invention additionally relates to processes for producing the particles and dosage form.

PRIOR ART

Cyclic nucleotide phosphodiesterase (PDE) inhibitors (specifically of type 4) are currently of special interest as a new generation of active ingredients for treating inflammatory disorders, especially inflammations of the airways such as asthma or airway obstructions (such as, for example, COPD=chronic obstructive pulmonary disease). A number of PDE 4 inhibitors is currently undergoing advanced clinical testing inter alia the PDE 4 inhibitor N-(3,5-dichloropyrid-4-yl)-3-cyclopropylmethoxy-4-difluoromethoxybenzamide (INN: roflumilast).

WO 03/070279 is related to a dosage form for oral administration of a PDE 4 inhibitor whose solubility is slight, which contain PVP as a binder. Inter alia the PDE 4 inhibitor N-(3,5-dichloropyrid-4-yl)-3-cyclopropylmethoxy-4-difluoromethoxybenzamide (INN: roflumilast) is mentioned in connection with the dosage form.

For pediatric or geriatric patients who cannot swallow a tablet, alternate administration forms such as a liquid suspension, oral granule formulation or orodispersible administration forms would be desirable to administer roflumilast. However roflumilast is observed to present an unpleasant taste respectively a numbness sensation, when exposed in the oral cavity. Overcoming unpleasant or bad taste of certain pharmaceutical active ingredients (drugs) is a continuous challenge for formulation scientist. A commonly used method to mask the taste of badly tasting drug substances and medications is the coating by a polymeric film, thereby avoiding the contact of the pharmaceutical active ingredient with the tongue and the oral cavity. Such coating can e.g. be performed on tablets, pellets, granulates and drug crystals. A commonly applied method to perform such a coating is in conventional pans (mainly for tablets) or in a fluidized bed process. In order to assure a proper coating in the fluidized bed, the coating process is typically performed by employing a so-called Wurster tube. In case of drug containing pellets, a multi-stage manufacturing process is necessary. Drug containing pellets can either be prepared by an extrusion process or by layering a drug substance on starter pellet cores made out of, e.g. cellulose or saccharose. For the latter method a solution or suspension of the drug substance is sprayed upon the starter pellets. In a second process step the coating layer is applied for taste masking. This is normally also done in a fluidized bed process by employing a Wurster tube. In the same way as pellets are coated, drug crystals, tablets or granulates can be coated.

WO 2005/013944 is related to a flavoured and taste-masked pharmaceutical composition comprising a plurality of pharmaceutically acceptable cores, such as microspheres, said pharmaceutically acceptable cores comprising etoricoxib, wherein the pharmaceutically acceptable cores are coated with a flavored taste-masking coating solution in a one-step coating process. However the process as described in WO 2005/013944 requires the provision of etoricoxib containing cores in a first step, which are then coated in a one-step coating process with a taste-masking coating solution or dispersion.

WO 02/45693 is related to new preparations for an active ingredient, which is present essentially uniformly dispersed in an excipient matrix composed of one or more excipients selected from the group of fatty alcohol, triglyceride, partial glyceride and fatty acid ester. In the case of active ingredients, which have an unpleasant taste or, for example, show a local anesthetic effect in the mouth after administration, it has been observed that an unpleasant taste of the active ingredient can be masked, and anesthetic effects in the mouth can be avoided, by preparations of the invention. Roflumilast is mentioned as active ingredient in examples 17 to 24 and 33.

It is therefore an object of the present invention to provide a taste masked pharmaceutical composition comprising roflumilast, which provides an effective taste masking and which can be prepared avoiding multi-stage manufacturing processes.

DESCRIPTION OF THE INVENTION

Surprisingly it has been found that the unpleasant taste of roflumilast can be effectively masked by providing roflumilast in a pharmaceutical dosage form based on coated particles comprising a suitable carrier and a coating layer surrounding the carrier, which coating layer comprises a suitable coating polymer, roflumilast and optionally further pharmaceutically acceptable excipients. The coated particles according to the invention advantageously can be prepared in a one-step process.

The present invention therefore relates to coated particles comprising a suitable carrier and a coating layer surrounding the carrier, which coating layer comprises a suitable coating polymer, optionally further pharmaceutically acceptable excipients and an active ingredient selected from the group of roflumilast, pharmaceutically acceptable salt of roflumilast, solvate or physiologically functional derivative thereof and mixtures thereof.

Roflumilast is the INN for a compound of the formula I

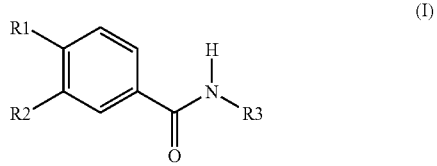

in which
R1 is difluoromethoxy,
R2 is cyclopropylmethoxy and
R3 is 3,5-dichloropyrid-4-yl.

This compound has the chemical name N-(3,5-dichloropyrid-4-yl)-3-cyclopropylmethoxy-4-difluoro-methoxybenzamide (INN: roflumilast). By the term "physiologically functional derivative" is meant a chemical derivative of roflumilast having the same physiological function as roflumilast, for example, by being convertible in the body thereto or by being an active metabolite of roflumilast. Physiological functional derivatives of roflumilast, which may be mentioned in connection with the invention are for example the N-oxide of roflumilast, and its salts and solvates. The N-oxide of roflumilast has the chemical name 3-cyclopropylmethoxy-4-difluoromethoxy-N-(3,5-dichloropyrid-4-yl-1-oxide)benzamide. The compound of the formula 1, its salts, the N-oxide, its salts and the use of these compounds as phosphodiesterase (PDE) 4 inhibitors are described in the international patent application WO 95/01338.

Roflumilast, pharmaceutically acceptable salt of roflumilast, solvate or physiologically functional derivative thereof and mixtures thereof is hereinafter also referred to as active ingredient.

Salts suitable for compounds of the formula I—depending on the substitution—are all acid addition salts but, in particular, all salts with bases. Particular mention may be made of the pharmacologically acceptable salts of the inorganic and organic acids and bases normally used in pharmaceutical technology. Pharmacologically unacceptable salts, which, for example, may be the initial products of the process for preparing the compounds of the invention on the industrial scale are converted into pharmacologically acceptable salts by processes known to the skilled worker. Those suitable on the one hand are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid, or 3-hydroxy-2-naphthoic acid, the acids being employed to prepare the salts in the equimolar ratio of amounts, or one differing therefrom—depending on whether the acid is monobasic or polybasic and depending on which salt is desired.

On the other hand, salts with bases are also particularly suitable. Examples of basic salts which may be mentioned are lithium, sodium, potassium, calcium, aluminium, magnesium, titanium, ammonium, meglumine or guanidinium salts, once again the bases being employed to prepare the salts in the equimolar ratio of amounts or one differing therefrom.

The coated particles according to the invention preferably have a mean particle size less than or equal to 2 mm and preferably equal to or less than 1 mm. It is particularly preferred to have a mean particle size less than or equal to 400 μm as coated particles of this size will provide a good mouthfeel in the oral cavity of a patient. By providing such a small particle size grittiness and a sandy mouthfeel can be avoided. In a preferred embodiment the coated particles according to the invention have a mean particle size in the range from 100 to 400 μm.

The coated particle according to the invention comprises a suitable carrier, which is surrounded by a coating layer. Suitable carriers according to the invention, which may be mentioned, are preferably based on inert excipients, which are customarily used in formulation technology as carriers. Excipients, which may preferably be mentioned, are selected from the group of mannitol, saccharose, lactose (e.g. lactose monohydrate), glucose, erythritol, xylitol, cellulose, microcrystalline cellulose, starch, croscarmellose sodium, crospovidone and mixtures thereof. Carriers according to the invention may be based on powders, granules, small beads, particles, pellets, starter pellets, nonpareils of suitable size composed of the above excipients or mixtures thereof. If a defined shape (e.g. a round shape) of the coated particles is desired it is advantageous to use carriers of a defined shape and size such as starter pellets made of microcrystalline cellulose or saccharose (nonpareilles). Carriers may also be obtained by (pre)granulation of the above excipients to provide carriers with a suitable size.

In one embodiment according to the invention the carrier is composed of microcrystalline cellulose, lactose monohydrate and croscarmellose sodium.

Carriers based on powders, granules, small beads, particles or pellets preferably have a mean particle size less than or equal to 2 mm and preferably equal to or less than 1 mm. It is particularly preferred to have a particle size less than or equal to 400 μm. In a preferred embodiment the carrier according to the invention has a suitable particle size, which after being layered with a coating layer results in coated particles which have a mean particle size in the range from 100 to 400 μm.

Suitable polymers for forming the coating layer surrounding the carrier in the particles according to the invention can be composed of water-soluble or water-insoluble coating polymers or mixtures thereof. Polymers which may be mentioned in connection with the invention are for example selected from the group of polyvinylpyrrolidon (PVP), cellulosic polymers such as ethylcellulose, hydroxypropylmethylcellulose (HPMC), hydroxypropyl cellulose (HPC), cellulose acetate phthalate, hydroxypropylmethylcellulosephthalate, acrylic polymers such as acrylate ammoniomethacrylate copolymer (Eudragit® RL100 or RS100 or Eudragit® RL30D or RS30D), ethylacrylate methylmethacrylate copolymer (Eudragit® NE30D), or methacrylic copolymers (Eudragit® L100-55 or Eudragit® L30D, Eudragit® E100, Eudragit® E PO), starch polymer, chitosan, and mixtures thereof.

In a preferred embodiment the coating polymer is selected from the group of water-soluble polymers, preferably selected from the group of starch polymer, hydroxypropylmethylcellulose (HPMC), hydroxypropyl cellulose (HPC), polyvinylpyrrolidon, chitosan, methacrylic copolymers (Eudragit® L100 or Eudragit® L100-55 or Eudragit® L30D-55, Eudragit® E100, Eudragit® E PO) and mixtures thereof. Polymers which show a pH dependent water solubility are particularly preferred. Eudragit® E PO (basic butylated methacrylate copolymer, Ph. Eur.) which is a copolymer based on dimethylaminoethyl methacrylate and neutral methacrylic esters, also referenced as poly(butyl methacrylate, (2-dimethyl aminoethyl) methacrylate, methyl methacrylate) 1:2:1 is particularly preferred (see Product specification Rohm, Pharma polymers and Handbook of Pharmaceutical Excipients, fourth edition, American Pharmaceutical Association). This polymer is swellable and permeable above pH 5 and soluble below pH 5. Due to these characteristics this polymer provides taste-masking in the mouth and release of roflumilast under acidic conditions in the stomach.

Depending on the polymer used, the active ingredient is either present in the coating layer in suspended form or dissolved, preferably homogeneously suspended or homogeneously dissolved. In the case of the active ingredient being present in suspended form, the active ingredient is present in the form of particles with a mean particle size in the range from 0.1-100 μm. Particles of the active ingredient having a mean particle size in the range from 1 to 10 μm can for example be obtained by micronization (milling by air jet) of the active ingredient of greater particle size or by a suitable crystallization process.

According to the invention the active ingredient is preferably embedded within the polymer of the coating layer surrounding the carrier. It is the embedding of the active ingredient within the coating layer, which provides the taste-masking. It is therefore not necessary to have a coating layer completely or continuously surrounding the carrier. Coated particles comprising a suitable carrier and a coating layer surrounding the carrier according to this invention do not necessarily need a continuous or complete coating layer to obtain a taste-masking.

Optionally further pharmaceutically acceptable excipients can be present in the coating layer of the coated particle according to the invention. Excipients, which may be mentioned in this connection are selected from the group of permeability agents, plasticizers, wetting agents and surfactants, anti-adhesives adhesives, flavouring agents, coloring agents and mixtures thereof.

Permeability agents, which may be mentioned are mannitol, lactose, water soluble polymers such as PVP, HPMC, HPC and polyethylene glycol.

Plasticizers, which may be mentioned are triethylcitrate, triacetine, stearic acid, dibutylsebacate, dibutylphthalate, glycerolmonostearate and polyethylene glycol.

Wetting agents and surfactants which may be mentioned are sodium laurylsulfate and polysorbates.

Anti-adhesives, which may be mentioned are magnesium stearate, talc, glycerolmonostearate, kaolin and Syloid™.

Coloring agents, which may be mentioned are iron oxides.

Preferred coated particles according to the invention have a coating layer comprising Eudragit® EPO, stearic acid, magnesium stearate, sodiumlauryl sulfate, roflumilast, pharmaceutically acceptable salt of roflumilast, solvate or physiologically functional derivative thereof and mixtures thereof.

Based on the weight of the coated particles the amount of the carrier by weight is in the range of 50-95%, preferably in the range of 70-95%.

Based on the weight of the coated particles the amount of the polymer coating by weight (including the polymer and all other excipients except the active ingredient) is in the range of 3-20%.

Based on the weight of the coated particles the amount by weight of the active ingredient is in the range of 0.1-2%, preferably 0.2-0.8%.

The taste masking efficiency can be adjusted by varying the ratio by weight of the active ingredient to the polymer coating (including the polymer and all other excipients). Conveniently the ratio is in the range of 1:5 to 1:40, preferably 1:10 to 1:25.

The coated particle according to the invention may additionally contain further coating layer, preferably a second, outer coating layer (overcoating) based on a water soluble polymer and optionally additional excipients to improve wettability and dispersibility of the particles in water. Suitable water soluble polymers which can be used for such overcoating are e.g. hydroxypropylmethylcellulose, hydroxyproylcellulose, polyvinylpyrrolidone, polyethylene glycol and mixtures thereof.

Based on the weight of the over-coated particles the amount by weight of the overcoating is in the range of 0.2-2%.

The coated particles according to the invention can be prepared by conventional techniques. To this end the active ingredient is suspended or dissolved in a coating polymer solution or dispersion optionally containing other suitable excipients. The polymer solution or dispersion can be on an aqueous base or on an organic base. Aqueous polymer solutions or dispersions are preferred. The polymer solution or dispersion can be prepared in a way known for those skilled in the area of pharmaceutical technology. The active ingredient is dispersed or dissolved within the polymer solution or dispersion. If necessary this can be done by stirring or the use of a turboemulsifier. This solution/dispersion can then be sprayed on the carrier for example by applying a fluidized bed process with conventional bottom spray technique with a Wurster tube or by a top spray technique. This process is particularly preferred when using a carrier based on excipients in powder, or granule form. If a round shape of the particles is desired (eg to obtain a better mouth feel or better flowability) starter pellets made of cellulose or saccharose can be used as carrier instead of the powder blend or granulate. Due to the embedding of roflumilast within the polymer a masking of the unpleasant taste is effectively achieved without the need for a continuous polymer film.

Optionally a second outer polymer coating can be applied on the coated particles by the same process as described above. The polymer solution or dispersion can then be sprayed on the coated particles for example by applying a fluidized bed process with conventional bottom spray technique with a Wurster tube or by a top spray technique.

The advantage of the process described herein is that there is not a multi-stage process necessary for achieving the taste-masking, but that taste-masked coated particles can be prepared by a single process step.

Further subject of the invention is therefore a process for the manufacturing of coated particles according to the invention comprising the following steps:
(a) providing a suspension or solution of the active ingredient in a coating polymer solution or dispersion, optionally containing other suitable excipients
(b) spraying the solution or dispersion of step (a) on the carrier to obtain coated particles; and
(c) optionally spraying a polymer solution or dispersion on the coated particles as overcoating The coated particles of the invention can then be used as basis for producing the dosage forms of the invention. The coated particles according to the invention can be either compressed to tablets, e.g. those that disintegrate rapidly in the mouth (orodispersible dosage form) or rapidly disperse in a glass of water. Alternatively the coated particles can be mixed with suitable excipients resulting in a powder for oral administration or for the preparation of a suspension for oral administration. These formulations can be applied in single dose packages. They can be poured directly in the mouth for the application or they can be dispersed prior to the application in water. A preparation of a suspension from the powder prior to the treatment period is also possible. In this case, the suspension can be stored for e.g. a treatment period of two weeks.

Orodispersible dosage form in connection with the invention is to be understood as dosage form, which when placed in the oral cavity disperses rapidly before being swallowed. After disintegration in the oral cavity the tablet constituents are swallowed and the drug substance is absorbed in the gastro intestinal tract. In one embodiment the dosage form according to the invention is therefore a rapidly disintegrating dosage form in the form of an orodispersible tablet comprising an effective amount of the active ingredient in form of coated particles according to the invention together with excipients which, on oral intake of the dosage form, bring about rapid disintegration of the dosage form in the oral cavity, and, where appropriate, further excipients. The dosage form preferably has a maximum disintegration time in water (at 37° C.) of 3 minutes, 2 minutes or 1 minute. (The disintegration time of the tablet can be determined according to standard procedures disclosed in pharmacopoeia monographs, preferably according to the European Pharmacopoeia $4^{th}$ edition). Further examples of excipients which may be mentioned are fillers, carriers, disintegrants, binders, effervescence systems, lubricants, colouring agents, sweeteners, aromas, flavourings, pH-modifiers and surface-active substances. Fillers or carriers suitable in connection with the orodispersible tablet according to the invention are, in particular, fillers such as, calcium silicate (Rxipients®), sugar alcohols such as mannitol (e.g. Pearlitol® or Parteck® M, Merck, Germany), sorbitol (e.g. Karion®), xylitol, erythritol (e.g. Erythritol DC, Cerestar, Belgium), or maltitol, starches such as corn starch, potato starch and wheat starch, microcrystalline cellulose, saccharides such as glucose, lactose, sucrose and dextrose, co-processed fillers such as Pharmaburst®, SPI Pharma, USA, Starlac™, Meggle, Germany.

The content (in per cent by weight based on the finished dosage form) of filler in the tablet according to the invention is advantageously from 1 to 99% by weight. The content of filler is preferably from 30 to 95% by weight, and the content is particularly preferably from 40 to 80% by weight.

If appropriate, disintegrants can be added. Disintegrants suitable according to the invention are, in particular, insoluble polyvinylpyrrolidone (insoluble PVP, crospovidone), sodium carboxymethyl starch, sodium carboxymethylcellulose croscarmellose sodium, alginic acid, and starches able to fulfill the function of a disintegrant (e.g. Starch 1500).

The content (in per cent by weight based on a tablet according to the invention) of disintegrant in the orodispersible, rapidly disintegrating tablet according to the invention can usually be from 0.5 to 30% by weight. The content of disintegrant is preferably from 1 to 15% by weight. The content of disintegrant is particularly preferably from 1 to 5% by weight.

Suitable lubricants, which may be mentioned are sodium stearyl fumarate, magnesium stearate, calcium stearate, stearic acid, talc and colloidal silica (Aerosil).

The content (in per cent by weight based on the finished dosage form) of lubricant in the rapidly disintegrating orodispersible tablet according to the invention is usually from 0.1 to 5% by weight. The content of lubricant is preferably from 0.2 to 3% by weight. The content of lubricant is particularly preferably from 0.5 to 2% by weight.

Binders suitable according to the invention are polyvinylpyrrolidone (PVP, Polyvidon® K25, Polyvidon® K90) or mixtures of PVP with polyvinyl acetate (e.g. Kollidon® 64), gelatin, corn starch paste, preswollen starches (Starch® 1500, Uni-Pure® WG220), hydroxypropylmethylcellulose (HPMC) or hydroxypropylcellulose (L-HPC).

The content (in per cent by weight based on the tablet according to the invention) of binder can be up to 10% by weight, and it can preferably be up to 5% by weight.

Suitable surface-active substances which may be mentioned are sodium lauryl sulfate or Tween® 20, Tween® 60 or Tween® 80.

It is also possible if desired for one or more flavours and sweeteners to be present in the dosage form according to the invention. It is possible thereby for example to achieve an improvement in taste. These substances are added in the usual amounts.

In a preferred embodiment of the invention, the orodispersible dosage form of the invention comprises coated particles of active ingredient, at least one filler, preferably on the basis of mannitol, optionally a disintegrant, a lubricant, a sweetener and a flavouring agent.

The orodispersible tablet can be produced by processes known to the skilled worker. The rapidly disintegrating tablet is preferably produced by
i) dry mixing of filler and/or disintegrant;
ii) production of granules of filler and binder and mixing of the granules with a disintegrant or
iii) dry granulation (briqueting or compacting) of one or more excipient components.

The coated particles are subsequently admixed to the mixtures obtained in i), ii) or iii) and then, if desired, flavors/flavoring substances and finally also one or more lubricants are admixed. The mixture obtained in this way can be compressed in a tablet press under conventional conditions.

In the case of dosage forms based on powders for oral administration or for the preparation of a suspension for oral administration, suitable excipients are, in particular, those excipients, which are normally used to produce suspensions. Particularly suitable according to the invention are excipients with which it is possible to produce a thickened base, such as thickeners. Examples of thickeners in connection with the invention are xanthan, substituted celluloses, polyvinylpyrrolidone (polyvidone types), sheet silicates, alginates, alginic acids or mixtures thereof. The proportion of thickener depends on the desired viscosity or consistency intended for the suspension ready for use. The proportion of xanthan, based on the suspension ready for use, is usually from 0.1 to 1% by weight. The proportion of substituted celluloses depends on the viscosity levels of the celluloses and is usually from 0.1 to 10% by weight based on the suspension ready for use. Examples of substituted celluloses of the invention, which may be mentioned are carboxymethylcellulose, methylcellulose, hydroxypropylmethylcellulose or hydroxypropylcellulose. The proportion of polyvinylpyrrolidone (polyvidone types) is normally from 0.1 to 10% by weight based on the suspension ready for use. Sheet silicates such as the veegum or bentonites can be employed alone or in combination with water-soluble thickeners. The total proportion of thickener is then advantageously from 0.1 to 7% by weight based on the suspension ready for use. Alginates and alginic acid are usually added in a proportion of from 0.1 to 10% by weight based on the suspension ready for use. Further pharmaceutical excipients preferably employed are insoluble, crosslinked polyvinylpyrrolidone (crospovidones) and microcrystalline cellulose. It is observed in this case, that a loose sediment forms and prevents agglomeration of the individual active ingredient units. Microcrystalline cellulose and crospovidone are normally employed in a proportion of from 0.5 to 5% by weight based on the suspension ready for use.

Other suitable excipients, which may be present in the powder for oral administration or for the preparation of a suspension of the invention are, for example, flavoring substances (such as flavors and sweeteners), pH-modifiers, preservatives or else emulsifiers. Flavors are added in usual amounts. Other flavoring substances by way of example are acids such as citric acid, sweeteners such as saccharin, aspartame, cyclamate sodium or maltol, which are added according to the desired result. Examples of emulsifiers are lecithins, sodium lauryl sulfate, Tweens® or Spans, which are normally added in a proportion of from 0.01 to 1% by weight. Preservatives such as benzoic acid, salts of benzoic acid, methyl 4-hydroxybenzoate, propyl 4-hydroxybenzoate, sorbic acid or salts thereof might also be added if needed. The proportion depends on the preservative used and is normally from 0.1 to 4% by weight based on the suspension ready for use.

Depending on the polymer used for the coating of the particles (i.e. in the case of polymers which have a pH dependent solubility) it can be necessary to add pH-modifiers in order to prevent the release of active ingredient in the suspension prior to administration. When basic polymers, such as Eudragit EPO or chitosan are used, the pH of the suspension preferably needs to be above pH 5. When an acidic polymer, such as Eudragit L, cellulose acetate phthalate or hydroxypropylmethylcellulose phthalate is used, the pH of the suspension preferably is below pH5. Suitable pH-modifiers are for example citric acid and its salts, tartaric acid and its salts, phosphoric acid and its salts and all other pharmacologically acceptable pH-modifiers.

The powder for the direct oral administration or for the preparation of the suspension of the invention is produced by techniques known to the skilled worker. Preferably the coated particles are blended with the other excipients. If single dose packages are the dosage form of choice, it might be also possible to fill first the coated granules into the sachet followed by the filling of the blend of the other excipients. Water is preferably used as dispersant for the preparation of the suspension prior to the use or prior to the treatment period.

The coated particles and the dosage forms according to the invention are described by way of examples below. The following examples explain the invention in more detail without restricting it.

EXAMPLES

1. Coated Granules
1.1 Preparation of the granulation suspension 1.51 g of sodium dodecylsulfate was dissolved in 125.87 g of water by stirring. After 5 min stirring 15.08 g of Eudragit® EPO was suspended. After another 10 min 2.26 g of stearic acid was added and the suspension was stirred for at least 5 hours. 5.28 g of magnesium stearate was added and suspended under stirring. Finally, 2.23 g of roflumilast micronized were suspended.

1.2 Preparation of the Coated Granules 94.5 g of microcrystalline cellulose, 94.5 g of lactose monohydrate and 10.5 g of croscarmellose sodium were mixed in a fluidized bed granulator. 59.62 g of the suspension prepared under 1.1 were sprayed upon the powder blend. In a typical process, the temperature of the fluidized powder is in the range of 25-35° C. The formulation avoids the numbness sensation normally observed, when the oral cavity is exposed to roflumilast formulations.

1.3 Preparation of Granulation Suspension and Granulation 3.02 g of sodium dodecylsulfate was dissolved in 251.74 g of water by stirring. After 5 min stirring 30.17 g of Eudragit EPO was suspended. After another 10 min 4.52 g of stearic acid was added and the suspension was stirred for at least 5 hours. 10.56 g of magnesium stearate was added and suspended under stirring. Finally, 2.23 g of roflumilast micronized were suspended. 119.24 g of the suspension was sprayed on a powder blend composed of 94.5 g of microcrystalline cellulose, 94.5 g of lactose monohydrate and 10.5 g of croscarmellose sodium in a fluidized bed apparatus.

1.4. Preparation of Granulation Suspension and Granulation 10 g of talcum was dispersed in 36.65 g of water under stirring. 33.33 g of Eudragit NE30D dispersion was added and mixed. Finally, 2.20 g of roflumilast micronized has been added. 94.5 g of microcrystalline cellulose, 94.5 g of lactose monohydrate and 10.5 g of croscarmellose sodium were mixed in a fluidized bed granulator. 59.62 g of the suspension were sprayed upon the powder blend.

2. Coated Pellets
2.1 Preparation of Pellets 118 g of the suspension prepared under 1.1 was sprayed upon 190 g of commercially available pellets made of cellulose (Cellets™) in a fluidized bed process. The size of the pellets was in the range of 100-200 μm and did not change significantly during the spraying process. The formulation avoids the numbness sensation normally observed, when the oral cavity is exposed to roflumilast formulations.

2.2. Preparation of Pellets with Additional Overcoating 1.2 g of HPMC 15 cp was dissolved in 46.35 g of water. 19.8 g of the solution was sprayed on 39.1 g of the coated pellets which were prepared according to 2.1. The pellets with overcoating can be dispersed easily in water without floating.

3. Dissolution Testing

Dissolution testing has been performed with the pellets prepared under 2.1. The dissolution conditions were the following:

Apparatus: USP paddle
Medium: Phosphate buffer pH6.8+0.1% SDS, 1000 ml, 37° C.
Rotation speed: 50 rpm The following amount of roflumilast was dissolved:

| | |
|---|---|
| 5 min | 2.3% |
| 15 min | 8.7% |
| 60 min | 35.0% |

When the same dissolution testing has been performed under acidic conditions (0.1N—HCl +0.1% SDS) completed dissolution was obtained after 30 min.

These data show that by the proposed manufacturing method a taste-masking can be obtained in the oral cavity, since the dissolution is low under neutral conditions.

4. Preparation of Dosage Forms
4.1 Preparation of Orodispersible Tablets 60 g of the granulate according to 1.3 is blended with 234 g of Pharmaburst™, 0.45 g of aspartame, 0.45 g of acesulfame potassium and 0.6 g of flavours. Finally 4.5 g of magnesium stearate were added. The blend is compressed to tablets. The disintegration time was less than 2 min.

4.2. Preparation of a Powder for the Preparation of an Oral Suspension.

3 g of xanthan, 12 g of crospovidone, 55 g of saccharose, 29.2 g of mannitol, 0.3 g of sodium laurylsulfate and 0.5 g of flavour were blended. 6.2 g of the over-coated pellets prepared under 2.2. were added. 1.00 g of the final blend was suspended in 20 ml of water prior to the administration.

INDUSTRIAL APPLICABILITY

The dosage forms of the invention can be employed for the treatment and prevention of all diseases regarded as treatable or preventable through the use of PDE 4 inhibitors. Selective cyclic nucleotide phosphodiesterase (PDE) inhibitors (specifically of type 4) are suitable on the one hand as bronchial therapeutic agents (for the treatment of airway obstructions owing to their dilating effect but also owing to their effect increasing the respiratory rate and respiratory drive) and for eliminating erectile dysfunction owing to the vasodilating effect, but on the other hand especially for the treatment of disorders, especially of an inflammatory nature, e.g. of the airways (asthma prophylaxis), of the skin, of the central nervous system, of the intestine, of the eyes and of the joints, which are promoted by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen free radicals and proteases. The pharmaceutical preparations of the invention can therefore be used in human and veterinary medicine for example for the treatment and prophylaxis of the following diseases: acute and chronic (especially inflammatory and allergen-induced) airway disorders of various etiologies (bronchitis, allergic bronchitis, bronchial asthma, COPD); dermatoses (especially of a proliferative, inflammatory and allergic nature) such as, for example, psoriasis (vulgaris), toxic and allergic contact eczema, atopic eczema, seborrhoic eczema, lichen simplex, sunburn, pruritus in the genitoanal region, alopecia areata, hypertrophic scars, discoid lupus erythematosus, follicular and extensive pyodermas, endogenous and exogenous acne, acne rosacea and other proliferative, inflammatory and allergic skin disorders; disorders based on excessive release of TNF an leukotrienes, e.g. disorders of the arthritic type (rheumatoid arthritis, rheumatoid spondylitis, osteoarthritis and other arthritic states), disorders of the immune system (AIDS, multiple sclerosis), types of shock [septic shock, endotoxin shock, gram-negative sepsis, toxic shock syndrome and ARDS (adult respiratory distress syndrome)] and generalized inflammations in the gastrointestinal region (Crohn's disease and ulcerative colitis); disorders based on allergic and/or chronic abnormal immunological reactions in the region of the upper airways (pharyngeal space, nose) and adjacent regions (paranasal sinuses, eyes), such as, for example, allergic rhinitis/sinusitis, chronic rhinitis/sinusitis, allergic conjunctivitis and nasal polyps; but also cardiac disorders which can be treated by PDE inhibitors, such as, for example, heart failure, or disorders which can be treated owing to the tissue-relaxant effect of PDE inhibitors, such as, for example, erectile dysfunction or colic of the kidneys and ureters connected with kidney stones; or else disorders of the CNS such as, for example, depressions or arteriosclerotic dementia.

The invention further relates to a method for the treatment of mammals, including humans, suffering from one of the abovementioned diseases. The method is characterized by administration of a therapeutically effective and pharmacologically suitable amount of roflumilast to the mammalian patient, roflumilast being present in a dosage form of the invention. The disease is preferably asthma or airway obstructions, especially COPD (=chronic obstructive pulmonary disease).

The dosage forms of the invention comprise the active ingredient in the dose customary for the treatment of the particular disease. The dosage of the active ingredient is of the order of magnitude customary for PDE inhibitors, it being possible to administer the daily dose in one or more dosage units. The normal dose on systemic therapy (oral) is between 0.001 mg and 3 mg per kilogram and day. Dosage forms preferred according to the invention contain from 0.01 mg to 5 mg of roflumilast, preferably from 0.05 mg to 2.5 mg, particularly preferably 0.1 mg to 0.5 mg of roflumilast per dosage unit. Examples of dosage form of the invention contain 0.1 mg, 0.125 mg, 0.25 mg and 0.5 mg of roflumilast per dosage unit. Normally, one or more than one dosage unit of the invention is administered once a day. If desired, it is also possible for one or more dosage units of the invention to be administered more than once a day.

The invention claimed is:

1. Coated particles comprising a carrier and a coating layer surrounding the carrier, which coating layer comprises i) a coating polymer comprising basic butylated methacrylate copolymer, which is a copolymer based on dimethylaminoethyl methacrylate and neutral methacrylic esters, ii) stearic acid, iii) magnesium stearate, iv) sodiumlauryl sulfate, and v) an active ingredient, which is the sole active ingredient, and is selected from the group consisting of roflumilast, a pharmaceutically acceptable salt of roflumilast, a solvate of roflumilast, a physiologically functional derivative of roflumilast and mixtures thereof, wherein the coated particles have a mean particle size less than or equal to 2 mm, or less than or equal to 1 mm.

2. Coated particle according to claim 1, wherein the active ingredient is roflumilast.

3. Coated particle according to claim 1, having a mean particle size in the range from 100 to 400 μm.

4. Coated particle according to claim 1, wherein the carrier is based on excipients selected from the group consisting of mannitol, saccharose, lactose, glucose, erythritol, xylitol, cellulose, microcrystalline cellulose, croscarmellose sodium, crospovidone and mixtures thereof.

5. Coated particle according to claim 4, wherein the carrier is in the form of a powder, granule, small bead, particle, pellet, starter pellet or nonpareil.

6. Coated particle according to claim 2, wherein roflumilast is suspended in the coating layer.

7. Coated particle according to claim 6, wherein the mean particle size of roflumilast suspended in the coating layer is in the range from 0.1 to 100 μm.

8. Coated particle according to claim 7, wherein the coating layer comprises further pharmaceutically acceptable excipients selected from the group consisting of permeability agents, plasticizers, wetting agents and surfactants, anti-adhesives, flavouring agents, coloring agents and mixtures thereof.

9. Coated particle according to claim 1, wherein the ratio by weight of the active ingredient selected from the group consisting of roflumilast, a pharmaceutically acceptable salt of roflumilast, a solvate of roflumilast, a physiologically functional derivative of roflumilast and mixtures thereof to the coating layer is in the range of 1:5 to 1:40.

10. Coated particle according to claim 1 additionally containing an outer overcoating.

11. A process for producing a coated particle according to claim 1, comprising the following steps:
(a) providing a suspension or solution of the active ingredient in a coating polymer solution or dispersion, optionally containing other pharmaceutically acceptable excipients; and
(b) spraying the solution or dispersion of step (a) on the carrier; and
(c) optionally spraying a polymer solution or dispersion on the coated particles of step (b).

12. Process according to claim 11, wherein in step (a) an aqueous suspension or solution is provided.

13. Process according to claim 11, wherein spraying is carried out applying a fluidized bed process with a Wurster tube or top spray technique.

14. Dosage form comprising a therapeutically effective amount of an active ingredient selected from the group consisting of roflumilast, a pharmaceutically acceptable salt of roflumilast, a solvate of roflumilast, a physiologically functional derivative of roflumilast and mixtures thereof in the form of coated particles according to claim 1 together with one or more pharmaceutically acceptable excipients.

15. Dosage form according to claim 14, which is a tablet, a powder for oral administration or a suspension for oral administration.

16. Dosage form according to claim 14, which is an orodispersible dosage form.

17. A method for the treatment of a disease regarded as treatable by PDE 4 inhibitors in a patient, comprising administering a dosage form as claimed in claim 14 to a patient in need thereof.

18. Coated particle according to claim 7, wherein the mean particle size of roflumilast suspended in the coating layer is in the range from 1 to 10 μm.

19. Coated particle according to claim 9, wherein the ratio by weight of the active ingredient selected from the group consisting of roflumilast, a pharmaceutically acceptable salt of roflumilast, a solvate of roflumilast, a physiologically functional derivative of roflumilast and mixtures thereof to the coating layer is in the range of 1:10 to 1:25.

20. The method according to claim 17, wherein the disease is selected from the group consisting of bronchitis, allergic bronchitis, bronchial asthma and COPD.

21. The method according to claim 20, wherein the disease is COPD.

\* \* \* \* \*